United States Patent
Di Francesco et al.

(10) Patent No.: US 8,183,216 B2
(45) Date of Patent: May 22, 2012

(54) NUCLEOSIDE DERIVATIVES AS INHIBITORS OF VIRAL POLYMERASES

(75) Inventors: Maria Emilia Di Francesco, Rome (IT); Vincenzo Summa, Rome (IT); Gabriella Dessole, Rome (IT)

(73) Assignee: Istituto Di Ricerche Di Biologia Molecolare P. Angeletti S.p.A., Rome (IT)

( * ) Notice: Subject to any disclaimer, the term of this patent is extended or adjusted under 35 U.S.C. 154(b) by 96 days.

(21) Appl. No.: 12/679,713

(22) PCT Filed: Sep. 16, 2008

(86) PCT No.: PCT/EP2008/062289
§ 371 (c)(1),
(2), (4) Date: Mar. 24, 2010

(87) PCT Pub. No.: WO2009/040269
PCT Pub. Date: Apr. 2, 2009

(65) Prior Publication Data
US 2010/0210581 A1  Aug. 19, 2010

(30) Foreign Application Priority Data
Sep. 24, 2007  (GB) .................................. 0718575.4

(51) Int. Cl.
*A01N 43/04* (2006.01)
*A61K 31/70* (2006.01)
*C07H 19/00* (2006.01)
*C07H 19/056* (2006.01)

(52) U.S. Cl. ........ 514/43; 536/27.1; 536/28.1; 536/28.7
(58) Field of Classification Search .................... None
See application file for complete search history.

(56) References Cited

U.S. PATENT DOCUMENTS

| | | | |
|---|---|---|---|
| 3,480,613 | A | 11/1969 | Walton et al. |
| 5,413,999 | A | 5/1995 | Vacca et al. |
| 2006/0252715 | A1 | 11/2006 | Keicher et al. |

FOREIGN PATENT DOCUMENTS

| | | |
|---|---|---|
| GB | 2337262 A | 11/1999 |
| WO | 97/41211 A1 | 11/1997 |
| WO | 98/17679 A1 | 4/1998 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A2 | 8/1999 |
| WO | 99/50230 A1 | 10/1999 |
| WO | 99/64442 A1 | 12/1999 |
| WO | 00/09543 A2 | 2/2000 |
| WO | 00/25780 A1 | 5/2000 |
| WO | 00/59929 A1 | 10/2000 |
| WO | 01/00622 A1 | 1/2001 |
| WO | 01/74768 A2 | 10/2001 |
| WO | 01/81325 A2 | 11/2001 |
| WO | 02/057287 A2 | 7/2002 |
| WO | 02/057425 A2 | 7/2002 |
| WO | 02/100415 A2 | 12/2002 |
| WO | 2005/003147 A2 | 1/2005 |
| WO | 2005/021568 A2 | 3/2005 |
| WO | 2006/065335 A2 | 6/2006 |
| WO | 2006/093986 A1 | 9/2006 |

OTHER PUBLICATIONS

Brain W. Dymock, "Emerging therapies for hepatitis C virus infection," 6 Emerging Drugs 13-42 (2001).
Anthony C. Allison & Elsie M. Eugui, "Immunosuppressive and other anti-rheumatic activities of mycophenolate mofetil," 44 Agents and Actions Supplements 165-88 (1993).
Joel Kirschbaum, "Amantadine," 12 Profiles of Drug Substances, Excipients and Related Methodology 1-36 (1983).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
J.O. Saunders & S.A. Raybuck, "Inosine Monophosphate Dehydrogenase: Consideration of Structure, Kinetics and Therapeutic Potential," 35 Ann. Rep. Med. Chem. 201-210 (2000).
L.B. Townsend et al., 33 J. Med Chem. 1984-1992 (1990).
W. Clark Still et al., "Rapid Chromatographic Technique for Preparative Separations with Moderate Resolution," 43(14) J. Org. Chem. 2923-25 (1978). V. Lohmann et al., "Replication of Subgenomic Hepatitis C Virus RNAs in a Hepatoma Cell Line," 285 Science 110-13 (1999).
J.P. Vacca et al., 91 Proc. Natl. Acad. Sci., 4095-4100 (1994).
H. Nakabayashi et al., 42 Cancer Res. 3858 (1982).
A.H. Cory et al., "Use of an aqueous soluble tetrazolium/formazan assay for cell growth assays in culture," 3(7) Cancer Commun. 207-212 (1991).
Sidwell & Huffman, "Use of disposable microtissue culture plates for antiviral and interferon induction studies," 22 Appl. Microbiol. 797-801 (1971).
N. H. McManus, "Microtiter Assay for Interferon: Microspectrophotometeric Quantitation of Cytopathic Effect", 31 Appl. Environ. Microbiol. 35-38 (1976).

*Primary Examiner* — Traviss C McIntosh, III
(74) *Attorney, Agent, or Firm* — Melissa B. Wenk; Sheldon O. Heber

(57) ABSTRACT

A class of nucleoside derivatives of formula (I), as defined herein, that are useful as inhibitors of RNA-dependent RNA viral replication and in particular HCV replication, are provided. Also provided are processes for the synthesis and use of such compounds for treating or preventing HCV infection. formula (I).

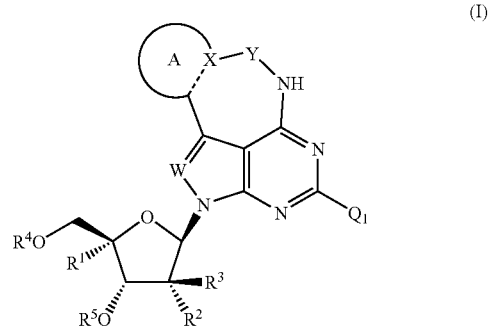

(I)

14 Claims, No Drawings

NUCLEOSIDE DERIVATIVES AS INHIBITORS OF VIRAL POLYMERASES

CROSS-REFERENCE TO RELATED APPLICATIONS

This application is a National Stage application of International Patent Application No. PCT/EP2008/062289, filed Sep. 16, 2008, which claims priority to British Provisional Patent Application No. GB 0718575.4, filed Sep. 24, 2007.

FIELD OF THE INVENTION

The present invention provides nucleoside derivatives which are inhibitors of viral polymerases. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

Different approaches to HCV therapy have been taken, which include the inhibition of viral serine proteinase (NS3 protease), helicase, and RNA-dependent RNA polymerase (NS5B), and the development of a vaccine Inhibition of HCV NS5B polymerase prevents formation of the double-stranded HCV RNA and therefore constitutes an attractive approach to the development of HCV-specific antiviral therapies.

Nucleoside compounds that exhibit activity as inhibitors of RNA-dependent RNA polymerase have already been disclosed in published International patent application nos. WO02/057287 and WO02/057425 (both Merck & Co., Inc. and Isis Pharmaceuticals, Inc.), WO2006/065335 (Merck & Co., Inc.), WO2005/003147 (Pharmasset, Ltd.) and WO02/100415 (F. Hoffmann-La Roche AG). Tricyclic nucleoside compounds that are useful in the treatment of viral infections have been disclosed in published International patent application nos. WO2005/021568 (Biota, Inc.) and WO2006/093986 (Genelabs Technologies, Inc.).

It has now been found that nucleoside compounds of the present invention and certain derivatives thereof are potent inhibitors of RNA-dependent RNA viral replication and in particular HCV replication. The nucleoside compounds of the present invention and phosphate derivatives thereof are inhibitors of RNA-dependent RNA viral polymerase and in particular HCV NS5B polymerase. The instant nucleoside compounds and derivatives thereof are useful to treat RNA-dependent RNA viral infection and in particular HCV infection.

DESCRIPTION OF THE INVENTION

In one embodiment, the present invention relates to compounds of structural formula (I) of the indicated stereochemical configuration:

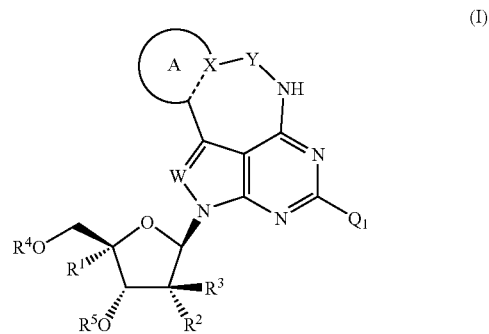

(I)

or a pharmaceutically acceptable salt thereof; wherein ring A is a 5- or 6-membered ring, optionally containing 1, 2 or 3 heteroatoms selected from N, O and S, and optionally containing one, two or three double bonds, and also optionally substituted by 1, 2 or 3 groups independently selected from CN, $C_{1-6}$alkyl, $C_{2-6}$alkenyl, $C_{2-6}$ alkynyl, $C_{1-6}$alkoxy, halogen, $C_{1-6}$haloalkyl, $C_{1-6}$haloalkoxy, $NR^xR^y$, $NR^zC(O)NR^xR^y$, $NR^xC(O)OR^y$, $OC(O)NR^xR^y$, $C(O)R^x$, $C(O)OR^x$, $C(O)NR^xR^y$, $SR^x$, $S(O)R^x$, $SO_2R^x$, $SO_2NR^xR^y$, wherein $R^x$, $R^y$ and $R^z$ are independently selected from hydrogen and $C_{1-6}$alkyl; and further optionally fused to another 5- or 6-membered ring, which ring optionally contains 1, 2 or 3 heteroatoms selected from N, O and S, and which ring optionally contains 1, 2 or 3 double bonds, and which ring is optionally substituted by 1, 2 or 3 groups independently selected from $C_{1-6}$alkyl, $C_{1-6}$alkoxy and halogen;

$Q^1$ is hydrogen or amino;

W is CH or amino;

X is CH, C or N;

the dotted bond represents a single bond when X is CH or N, or the dotted bond represents a double bond when X is C;

Y is C=O or $CH_2$;

$R^1$ is hydrogen, methyl, hydroxymethyl, fluoromethyl or $N_3$;

$R^2$ and $R^3$ are independently hydrogen, fluorine, hydroxy, $C_{1-4}$alkyl or $C_{1-4}$alkoxy;

$R^4$ is hydrogen, $PO_3H_2$, $P_2O_6H_3$, $P_3O_9H_4$ or a group $R^6$ wherein $R^6$ is $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl or a monophosphate prodrug residue of the formula

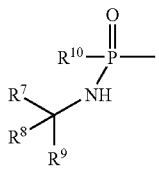

wherein $R^7$ is hydrogen, $C_{1-6}$alkyl optionally substituted with one substituent selected from the group consisting of fluoro, hydroxy, methoxy, amino, carboxy, carbamoyl, guanidino, mercapto, methylthio, 1H-imidazolyl, and 1H-indol-3-yl; or $R^7$ is phenyl, benzyl or phenethyl each optionally substituted with one to two substituents independently selected from the group consisting of halogen, hydroxy, and methoxy;

$R^8$ is hydrogen or methyl;

or $R^7$ and $R^8$ together with the carbon atom to which they attached form a 3- to 6-membered aliphatic spirocyclic ring system;

$R^9$ is aryl, arylalkyl, heteroaryl or

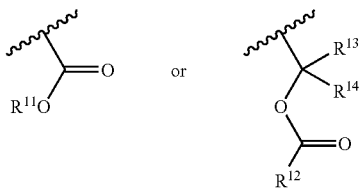

wherein $R^{11}$ is $C_{1-16}$alkyl, $C_{2-20}$alkenyl, $(CH_2)_{0-4}C_{7-9}$cycloalkyl, $(CH_2)_{0-4}C_{3-9}$cycloalkenyl or adamantly each optionally substituted with one to three substituents independently selected from halogen, hydroxy, carboxy, $C_{1-4}$alkoxy, trifluoromethyl and $(CH_2)_{0-4}NR^{15}R^{16}$ wherein $R^{15}$ and $R^{16}$ are independently selected from hydrogen and $C_{1-6}$alkyl; or $R^{15}$ and $R^{16}$, together with the nitrogen atom to which they are attached form a 4- to 7-membered heterocyclic ring optionally containing 1 or 2 more heteroatoms selected from N, O and S, which ring is optionally substituted by $C_{1-6}$ alkyl;

$R^{10}$ is hydroxy or a group $OR^{16}$ wherein $R^{16}$ is $CH_2OC(O)R^{17}$ or $CH_2CH_2SR^{17}$ where $R^{17}$ is $C_{1-6}$ alkylcarbonyl optionally substituted by a hydroxyl group or $R^{16}$ is $(CH_2)_{2-4}$—O—$(CH_2)_{1-17}CH_3$, or an aromatic ring selected from phenyl, naphthyl, pyridinyl, pyrimidinyl, pyrazinyl, pyridazinyl, indolyl, quinolinyl, or isoquinolinyl, wherein the aromatic ring is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl; or $R^{10}$ and $R^5$ form a bond to make a cyclic phosphate group;

$R^{12}$ is $C_{6-16}$alkyl, $C_{2-20}$alkenyl, $(CH_2)_{0-2}C_{7-9}$cycloalkyl, $(CH_2)_{0-2}C_{3-9}$cycloalkenyl, $OC_{1-6}$alkyl or adamantyl; and $R^{13}$ and $R^{14}$ are independently selected from hydrogen and $C_{1-6}$alkyl; or $R^{13}$ and $R^{14}$ together with the carbon atom to which they attached form a 3- to 6-membered aliphatic spirocyclic ring system;

$R^5$ is hydrogen or methyl, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl and an amino acyl residue of structural formula:

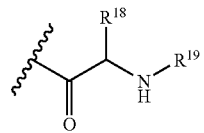

wherein $R^{18}$ is hydrogen, $C_{1-5}$ alkyl or phenyl$C_{0-2}$ alkyl; and $R^{19}$ is hydrogen, $C_{1-4}$ alkyl, $C_{1-4}$ alkylsulfonyl or phenyl$C_{0-2}$ alkylsulfonyl, or a group $COR^{20}$ wherein $R^{20}$ is $C_{1-4}$ alkyl optionally substituted by phenyl, $C_{1-4}$ alkoxy optionally substituted by phenyl, $C_{1-4}$alkylamino optionally substituted by $C_{1-4}$ alkyl optionally substituted by phenyl.

Preferably W is CH.

Preferably $Q^1$ is hydrogen.

Suitably $R^7$ is hydrogen, methyl or benzyl; more suitably hydrogen or methyl; $R^8$ is hydrogen or methyl; more suitably hydrogen; $R^9$ is Ph, $CO_2R^{11}$ or $CR^{13}R^{14}OC(O)R^{12}$ and $R^{10}$ is hydroxyl or $OR^{16}$; wherein $R^{16}$ is an aromatic or heteroaromatic ring or $CH_2CH_2SR^{17}$, where $R^{17}$ is $C_1$-$C_6$ alkylcarbonyl, optionally substituted with a hydroxyl group; more suitably $R^{10}$ is hydroxyl, O-phenyl or $CH_2CH_2S$—$C_1$-$C_6$-alkylcarbonyl optionally substituted with a hydroxyl group; most suitably $R^{10}$ is hydroxyl or $CH_2CH_2S$ S-tert-butylcarbonyl or $CH_2CH_2S$-hydroxy-tert-butylcarbonyl.

Suitably $R^{11}$ is $C_1$-$C_{16}$ alkyl, preferably $C_7$-$C_{16}$ alkyl

Suitably $R^{12}$ is $C_{1-6}$ alkyl, preferably $C_7$-$C_{16}$ alkyl; and $R^{13}$ and $R^{14}$ are hydrogens.

In one embodiment, the present invention relates to compounds of structural formula (Ia) of the indicated stereochemical configuration:

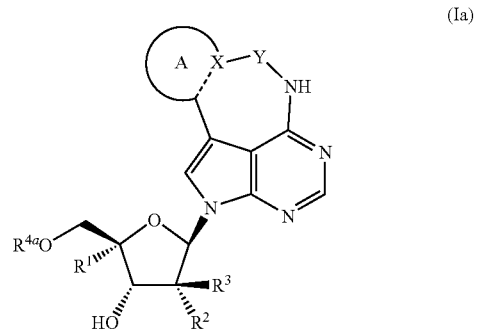

(Ia)

or a pharmaceutically acceptable salt thereof; wherein:

X, Y, $R^1$, $R^2$, $R^3$ and ring A are as hereinbefore defined;

$R^{4a}$ is hydrogen, $C(O)C_{1-10}$alkyl, $PO_3H_2$, $P_2O_6H_3$, $P_3O_9H_4$ or $P(O)R^aR^b$; wherein $R^a$ and $R^b$ are each independently hydroxy, OAr, $OCH_2CH_2SC(=O)C_{1-4}$alkyl, $OCH_2CH_2SC(=O)C_{1-4}$hydroxyalkyl, $OCH_2O(C=O)OC_{1-4}$alkyl, $NHCR^cR^dCO_2R^e$, $NR^cR^d$, $OCH(C_{1-4}$alkyl$)O(C=O)C_{1-4}$alkyl,

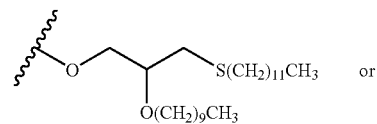

or

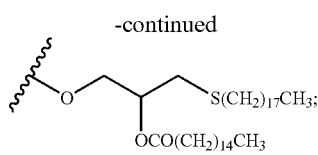

Ar is phenyl, naphythyl, pyridinyl, pyrimidinyl, pyrazinyl, pyridazinyl, indolyl, quinolinyl or isoquinolinyl, wherein Ar is optionally substituted with one to five substituents independently selected from the group consisting of halogen, $C_{1-4}$alkyl, $C_{1-4}$alkoxy, $C_{1-4}$alkylthio, cyano, nitro, amino, carboxy, trifluoromethyl, trifluoromethoxy, $C_{1-4}$alkylamino, di($C_{1-4}$alkyl)amino, $C_{1-4}$alkylcarbonyl, $C_{1-4}$alkylcarbonyloxy and $C_{1-4}$alkyloxycarbonyl;

$R^c$ is hydrogen, $C_{1-6}$alkyl, phenyl or benzyl, wherein alkyl is optionally substituted with one substituent selected from fluorine, hydroxy, methoxy, amino, carboxy, carbamoyl, guanidino, mercapto, methylthio, 1H-imidazolyl, and 1H-indol-3-yl, and wherein phenyl and benzyl are optionally substituted with one or two substituents independently selected from halogen, hydroxy or methoxy;

$R^d$ is hydrogen or methyl;

or $R^c$ and $R^d$ together with the carbon atom to which they are attached from a 3- to 6-membered aliphatic spirocyclic ring system;

$R^e$ is hydrogen, $C_{1-16}$alkyl, $C_{2-20}$alkenyl, $(CH_2)_{0-2}C_{3-6}$cycloalkyl, phenyl, benzyl or adamantyl; wherein alkyl, alkenyl, cycloalkyl and adamantyl are optionally substituted with one to three substituents independently selected from halogen, hydroxy, carboxy, $C_{1-4}$alkoxy; and wherein phenyl and benzyl are optionally substituted with one to three substituents independently selected from halogen, hydroxy, cyano, $C_{1-4}$alkoxy, trifluoromethyl and trifluoromethoxy.

In one embodiment of the present invention, ring A is a 5- or 6-membered ring, optionally containing 1, 2 or 3 heteroatoms selected from N, O and S, and optionally containing one, two or three double bonds. Preferably, ring A is a 5- or 6-membered ring, optionally containing 1 or 2 heteroatoms selected from N, O and S, and optionally containing one, two or three double bonds. More preferably, ring A is a 5- or 6-membered ring, optionally containing one heteroatom selected from N, O and S, and optionally containing two or three double bonds. Examples of suitable A groups are phenyl and thienyl.

In another embodiment of the present invention, X is C and the dotted bond represents a double bond.

In another embodiment of the present invention, X is N and the dotted bond represents a single bond.

In another embodiment of the present invention, $R^1$ is hydrogen or $N_3$. Preferably, $R^1$ is hydrogen.

In another embodiment of the present invention, $R^2$ is hydrogen, fluorine or hydroxy. Preferably, $R^2$ is fluorine or hydroxy. More preferably, $R^2$ is hydroxy.

In another embodiment of the present invention, $R^3$ is hydrogen, fluorine, hydroxy or methyl. Preferably, $R^3$ is fluorine or methyl. More preferably, $R^3$ is methyl.

In another embodiment of the present invention, $R^4$ is hydrogen, $C(O)C_{1-10}$alkyl, $PO_3H_2$, $P_2O_6H_3$ or $P_3O_9H_4$. Preferably, $R^4$ is hydrogen, $PO_3H_2$, $P_2O_6H_3$ or $P_3O_9H_4$. More preferably, $R^4$ is hydrogen or $P_3O_9H_4$.

In another embodiment of the present invention, there is provided the compound of structural formula (II) of the indicated sterochemical configuration:

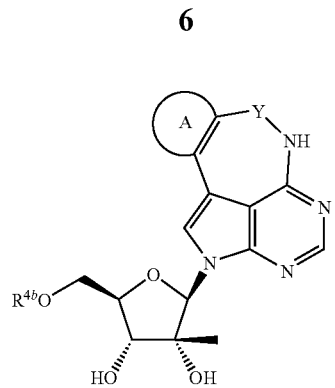

(III)

or a pharmaceutically acceptable salt thereof;

wherein Y, $R^1$, $R^2$ and $R^3$ are as defined in relation to formula (I), $R^{4b}$ is hydrogen, $C(O)C_{1-10}$alkyl, $PO_3H_2$, $P_2O_6H_3$, $P_3O_9H_4$ or $P(O)R^aR^b$; where $R^a$ and $R^b$ are each independently hydroxy, $OCH_2CH_2SC(=O)C_{1-4}$alkyl, $OCH_2O(C=O)OC_{1-4}$alkyl, OPh, $NHCHMeCO_2Et$, $OCH(C_{1-4}alkyl)O(C=O)C_{1-4}$alkyl,

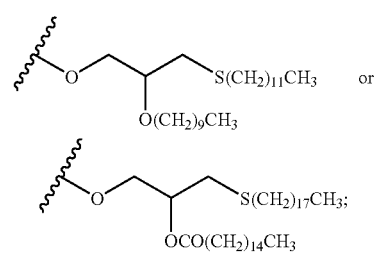

and ring A is a 5- or 6-membered ring, optionally containing 1 or 2 heteroatoms selected from N, O and S, and containing one, two or three double bonds.

In another embodiment of the present invention, there is provided the compound of structural formula (III) of the indicated stereochemical configuration:

(III)

or a pharmaceutically acceptable salt thereof;

wherein ring A, Y and $R^{4b}$ are as defined in relation to formula (II).

Illustrative but non-limiting examples of compounds of the present invention of structural formula (I) are the following:

2-(2-C-methyl-beta-D-ribofuranosyl)-2,6-dihydro-7H-2,3, 5,6-tetraazadibenzo[C,D,H]azulen-7-one, 2-(2-C-methyl-beta-D-ribofuranosyl)-6,7-dihydro-2H-2,3, 5,6-tetraazadibenzo[cd,h]azulene, 2-(2-C-methyl-beta-D-ribofuranosyl)-2,6-dihydro-7H-8-thia-2,3,5,6-tetraazabenzo[CD]cyclopenta[H]azulen-7-one, 2-(2-C-methyl-beta-D-ribofuranosyl)-6,7-dihydro-2H-8-thia-2,3,5,6-tetraazabenzo[CD]cyclopenta[H]azulene, 2-[5-O-(hydroxy{[hydroxy(phosphonooxy)phosphoryl]oxy}phosphoryl)-2-C-methyl-beta-D-ribofuranosyl]-2,6-dihydro-7H-2,3,5,6-tetraazadibenzo[cd,h]azulen-7-one, 2-[5-O-(hydroxy{[hydroxy(phosphonooxy)phosphoryl]oxy}phosphoryl)-2-C-methyl-beta-D-ribofuranosyl]-6,7-dihydro-2H-2,3,5,6-tetraazadibenzo[cd,h]azulene, 2-[5-O-(hydroxy{[hydroxy(phosphonooxy)phosphoryl]oxy}phosphoryl)-2-C-methyl-beta-D-ribofuranosyl]-6,7-dihydro-2H-8-thia-2,3,5,6-tetraazabenzo[cd]cyclopenta[h]azulene, 2-[5-O-(hydroxy{[hydroxy(phosphonooxy)phosphoryl]oxy}phosphoryl)-2-C-methyl-beta-D-ribofuranosyl]-2,6-dihydro-7H-8-thia-2,3,5,6-tetraazabenzo[cd]cyclopenta[h]azulen-7-one, and pharmaceutically acceptable salts thereof.

In another aspect of the present invention, the nucleoside compounds of the present invention are useful as inhibitors of positive-sense single-stranded RNA-dependent RNA viral polymerase, inhibitors of positive-sense single-stranded RNA-dependent RNA viral replication, and/or for the treatment of positive-sense single-stranded RNA-dependent RNA viral infection. In one embodiment, the positive-sense single-stranded RNA-dependent RNA virus is a Flaviviridae virus or a Picornaviridae virus. Preferably, the Picornaviridae virus is a rhinovirus, a poliovirus, or a hepatitis A virus. Also preferably, the Flaviviridae virus is selected from the group consisting of hepatitis C virus, yellow fever virus, dengue virus, West Nile virus, Japanese encephalitis virus, Banzi virus, and bovine viral diarrhea virus (BVDV). More preferably, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect, the RNA-dependent RNA viral polymerase is a positive-sense single-stranded RNA-dependent RNA viral polymerase. Preferably, the positive-sense single-stranded RNA-dependent RNA viral polymerase is a Flaviviridae viral polymerase or a Picornaviridae viral polymerase. More preferably, the Picornaviridae viral polymerase is rhinovirus polymerase, poliovirus polymerase, or hepatitis A virus polymerase. Also more preferably, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. Most preferably, the Flaviviridae viral polymerase is hepatitis C virus polymerase.

In another embodiment of this aspect, the RNA-dependent RNA viral replication is a positive-sense single-stranded RNA-dependent RNA viral replication. Preferably, the positive-sense single-stranded RNA-dependent RNA viral replication is Flaviviridae viral replication or Picornaviridae viral replication. More preferably, the Picornaviridae viral replication is rhinovirus replication, poliovirus replication, or hepatitis A virus replication. Also more preferably, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. Most preferably, the Flaviviridae viral replication is hepatitis C virus replication.

In a further embodiment of this aspect, the RNA-dependent RNA viral infection is a positive-sense single-stranded RNA-dependent viral infection. Preferably, the positive-sense single-stranded RNA-dependent RNA viral infection is Flaviviridae viral infection or Picornaviridae viral infection. More preferably, the Picornaviridae viral infection is rhinovirus infection, poliovirus infection, or hepatitis A virus infection. Also more preferably, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. Most preferably, the Flaviviridae viral infection is hepatitis C virus infection.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkynes of two to six total carbon atoms, or any number within this range (e.g., ethynyl, propynyl, butyryl, pentynyl, etc.).

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl, or cyclooctyl).

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.]. The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The terms "halogen" and "halo" are intended to include the halogen atoms fluorine, chlorine, bromine and iodine.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients.

Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, thymosin alpha-1, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine is an amidino analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease, such as LY570310 (VX-950). HCV NS3 serine protease is an essential viral enzyme and has been described to be an excellent target for inhibition of HCV replication. Both substrate and non-substrate based inhibitors of HCV NS3 protease inhibitors are disclosed in WO 98/17679, WO 98/22496, WO 98/46630, WO 99/07733, WO 99/07734, WO 99/38888, WO 99/50230, WO 99/64442, WO 00/09543, WO 00/59929, WO 01/74768, WO 01/81325, and GB-2337262. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13-42 (2001).

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622, (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O' kuru, et al., *J. Org. Chem.*, 62: 1754-1759 (1997); M. S. Wolfe, et al., *Tetrahedron Lett.*, 36: 7611-7614 (1995); and U.S. Pat. No. 3,480,613 (Nov. 25, 1969), the contents of which are incorporated by reference in their entirety. Such 2'-C-branched ribonucleosides include, but are not limited to, 2'-C-methyl-cytidine, 2'-C-methyl-adenosine, 2'-C-methyl-guanosine, and 9-(2-C-methyl-β-D-ribofuranosyl)-2,6-diaminopurine.

By "pharmaceutically acceptable" is meant that the carrier, diluent, or excipient must be compatible with the other ingredients of the formulation and not deleterious to the recipient thereof.

Also included within the present invention are pharmaceutical compositions comprising the nucleoside compounds and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase in particular HCV NS5B polymerase comprising an effective amount of a compound of this invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O, Saunders and S. A. Raybuck, "Inosine Monophosphate Dehydrogenase Consideration of Structure, Kinetics, and Therapeutic Potential," *Ann. Rep. Med. Chem.*, 35: 201-210 (2000).

Another aspect of the present invention provides for the use of the nucleoside compounds and derivatives thereof of the present invention and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the nucleoside compounds and derivatives thereof of the present invention and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formulae I, IV, and XII are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend nucleoside derivatives having the β-D stereochemical configuration for the five-membered furanose ring as depicted in the structural formula below, that is, nucleoside compounds in which the substituents at C-1 and C-4 of the five-membered furanose ring have the β-stereochemical configuration ("up" orientation as denoted by a bold line).

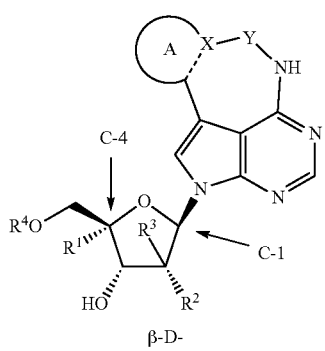

β-D-

The stereochemistry of the substituents at the C-2 and C-3 positions of the furanose ring of the compounds of the present invention is denoted either by a dashed line which signifies that the substituent, for example $R^2$ in structural formula I, has the α (substituent "down") configuration or a squiggly line which signifies that the substituent can have either the α (substituent "down") or β (substituent "up") configuration.

Compounds of structural formula I may be separated into their individual diastereoisomers by, for example, fractional crystallization from a suitable solvent, for example methanol or ethyl acetate or a mixture thereof, or via chiral chromatography using an optically active stationary phase.

Alternatively, any stereoisomer of a compound of structural formula I may be obtained by stereospecific synthesis using optically pure starting materials or reagents of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Preparation of the Nucleoside Compounds and Derivatives of the Invention

The nucleoside compounds and derivatives thereof of the present invention can be prepared following synthetic methodologies well-established in the practice of nucleoside and nucleotide chemistry. Reference is made to the following text for a description of synthetic methods used in the preparation of the compounds of the present invention: "Chemistry of Nucleosides and Nucleotides," L. B. Townsend, ed., Vols. 1-3, Plenum Press, 1988, which is incorporated by reference herein in its entirety.

General Description of Synthesis

The compounds of the present invention may be prepared as outlined in Schemes 1 to 4.

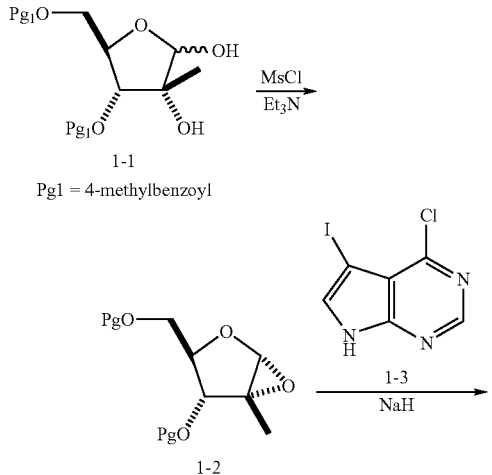

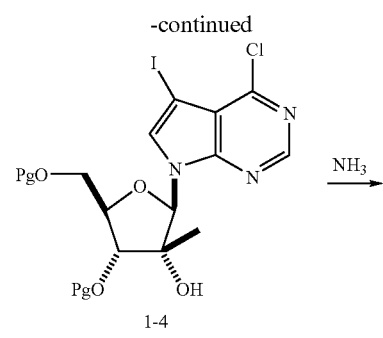

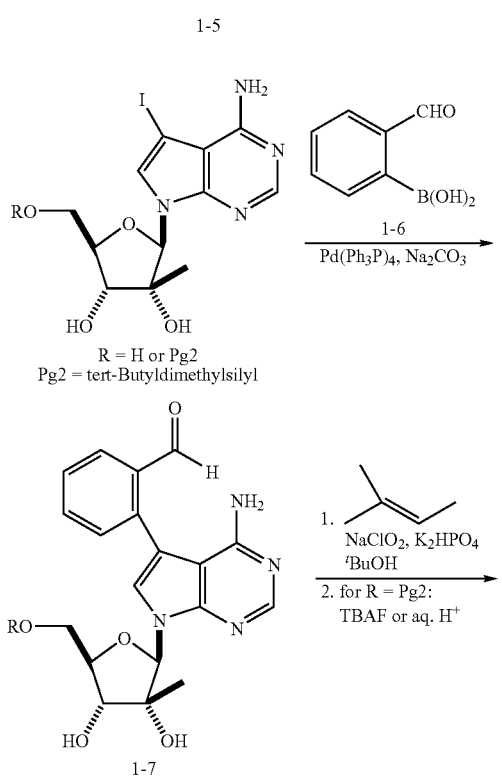

Scheme 1 describes the synthesis of 2-(2-C-methyl-β-D-ribofuranosyl)-2,6-dihydro-7H-2,3,5,6-tetraazadibenzo[C,D,H]azulen-7-one (entry 1, Table A) and related compounds. A suitable starting material for the synthesis of the compounds of the present invention can be nucleoside 1-5, whose synthesis is also described in Scheme 1. 4-chloro-5-iodo-7H-pyrrolo[2,3-d]pyrimidine 1-3 (prepared as described by Townsend, L. B. et al., *J. Med. Chem.* 1990, 33, 1984-1992) can be reacted with a ribose derivative such as 1-2 according to the methods described in WO 2004/072090 (also including the preparation of 1-1). 1-5 can then be optionally protected on the primary hydroxy group with a silicon containing moiety (t-butyl-dimethyl-silyl or similar) before undergoing Suzuki-Miyaura coupling with a boronic acid such as 1-6 or an equivalent reagent, either commercially available or prepared using methods known in the art. Oxidation of 1-7 using Lindgren conditions or an equivalent method can then afford 2-(2-C-methyl-β-D-ribofuranosyl)-2,6-dihydro-7H-2,3,5,6-tetraazadibenzo[C,D,H]azulen-7-one 1-8 directly or after removal of the silylated protecting group if present.

Scheme 2

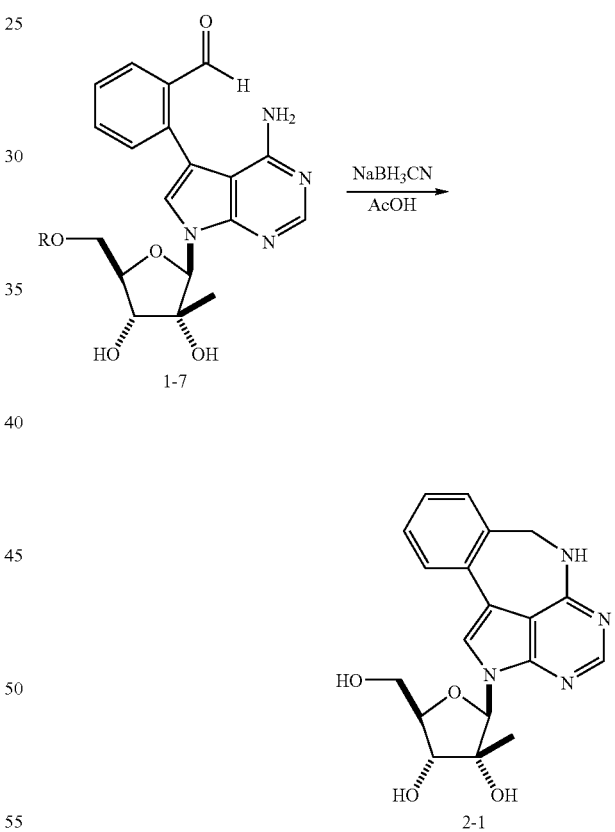

Scheme 2 describes the synthesis of 2-(2-C-methyl-β-D-ribofuranosyl)-6,7-dihydro-2H-2,3,5,6-tetraazadibenzo[cd,h]azulene (entry 2, Table A) and related compounds. Aldehyde 1-7, obtained as described in Scheme 1, can be converted to 2-(2-C-methyl-β-D-ribofuranosyl)-6,7-dihydro-2H-2,3,5,6-tetraazadibenzo[cd,h]azulene 2-1 by reductive amination employing sodium cyanoborohydride or an equivalent reagent.

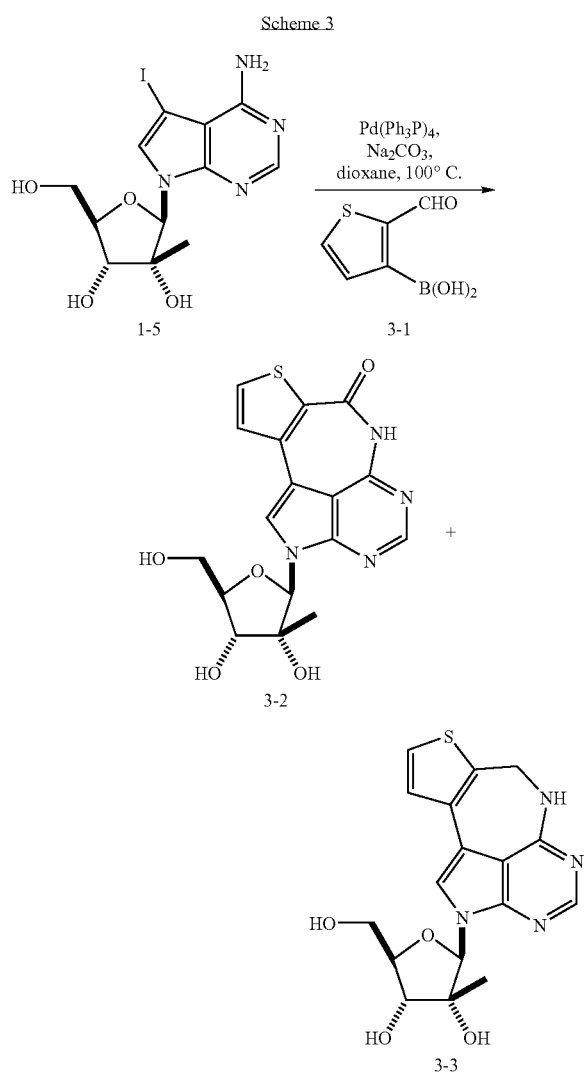

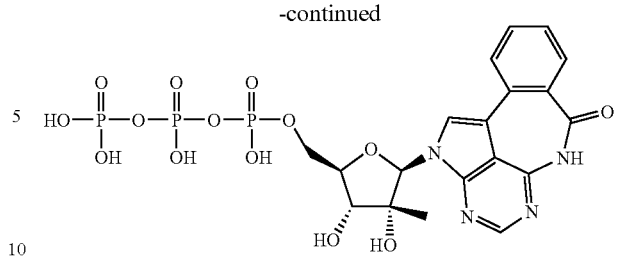

A further possible way to obtain compounds described in the present invention is shown in Scheme 3. For example, 2-(2-C-methyl-β-D-ribofuranosyl)-2,6-dihydro-7H-8-thia-2,3,5,6-tetraazabenzo[CD]cyclopenta[H]azulen-7-one 3-2 (entry 3, Table A) and 2-(2-C-methyl-(3-D-ribofuranosyl)-6,7-dihydro-2H-8-thia-2,3,5,6-tetraazabenzo[CD]cyclopenta[H]azulene 3-3 (entry 4, Table A) can be obtained by Suzuki-Miyaura coupling of 1-5 with a boronic acid such as 3-1.

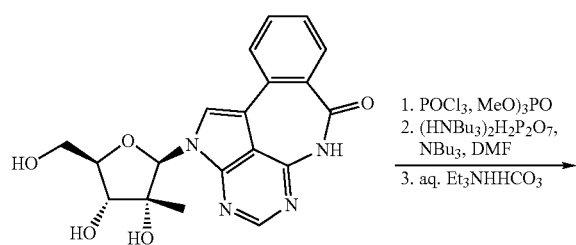

Scheme 4 describes the preparation of 2-[5-O-(hydroxy{[hydroxy(phosphonooxy)phosphoryl]oxy}phosphoryl)-2-C-methyl-β-D-ribofuranosyl]-2,6-dihydro-7H-2,3,5,6-tetraazadibenzo[cd,h]azulen-7-one 4-1 (entry 5, Table A) and related compounds by treatment of 2-(2-C-methyl-β-D-ribofuranosyl)-2,6-dihydro-7H-2,3,5,6-tetraazadibenzo[C,D,H]azulen-7-one or analogues thereof with phosphorous oxychloride followed by trimethyl phosphate, bis tributylammonium pyrophosphate and tributylamine.

General Procedures

All solvents were obtained from commercial sources and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on semi-automated flash chromatography systems utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H nmr spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; br, broad, and combinations thereof); coupling constant(s) in hertz; number of protons. Mass spectral (MS) data were obtained on a Perkin Elmer API 100, or Waters Micromass ZQ, operating in negative (ES$^-$) or positive (ES$^+$) ionization mode and results are reported as the ratio of mass over charge (m/z). Preparative scale HPLC separations were carried out on: 1) Shimadzu LC-8A separation module, equipped with a Shimadzu SPDC-10AV absorption detector; 2) Automated (mass-triggered) RP-HPLC Waters Micromass system, incorporating a 2525 pump module, a Micromass ZMD detector, and a 2767 collection module, operating under Fraction Lynx software. In both cases the stationary phase employed was a Simmetry C$_{18}$ column (7 μm, 19×300 mm), an Atlantis Prep dC18 (19×250 mm) or a XBridge (5 μm, 19×150 mm). Unless otherwise stated, the mobile phase comprised a linear gradient of binary mixture of MeCN (containing 0.1% TFA) and water (containing 0.1% TFA), using flow rates between 15 and 25 mL/min.

The following abbreviations are used in the Schemes and Examples: AcOH: acetic acid; aq.: aqueous; bs: broad singlet;

bt: broad triplet; DBU: 1,8-diazabicyclo[5.4.0]undec-7-ene; DIPEA: diisopropylethyl amine; DMF: dimethylformamide; DMSO: dimethylsulfoxide; eq.: equivalent(s); Et$_2$O: diethyl ether; EtOAc: ethyl acetate; EtOH: ethanol; (HNBu$_3$)$_2$H$_2$P$_2$O$_7$: bis tributylammonium pyrophosphate; h: hour(s); M: molar; MeCN: acetonitrile; MeOH: methanol; (MeO)$_3$PO: trimethyl phosphate; min: minutes; NaBH$_3$CN: sodium cyanoborohydride; NBu$_3$: tributylamine; NMP: 1-methyl-2-pyrrolidinone; Pd (PPh$_3$)$_4$: tetrakis(triphenylphosphine)palladium (0); PE: petroleum ether; P(O)Cl$_3$: phosphorous oxychloride; RP-HPLC: reversed phase high-performance liquid chromatography; RT: room temperature; SPE: solid phase extraction; TBDMS: tert-butyldimethylsilyl; TEA: triethylamine; TFA: trifluoroacetic acid; THF: tetrahydrofuran.

The examples below provide citations to literature publications, which contain details for the preparation of final compounds or intermediates employed in the preparation of final compounds of the present invention. The nucleoside compounds of the present invention were prepared according to procedures detailed in the following examples. The examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

REPRESENTATIVE EXAMPLES

Example 1

Entry 1, Table A 2-(2-C-methyl-β-D-ribofuranosyl)-2,6-dihydro-7H-2,3,5,6-tetraazadibenzo[C,D,H]azulen-7-one

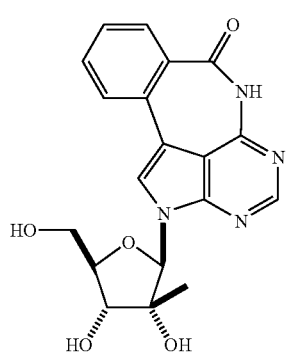

Pd(Ph$_3$P)$_4$ (0.1 eq) was added to a solution of 5-iodo-7-(2-C-methyl-β-D-ribofuranosyl)-7H-pyrrolo[2,3-c/]pyrimidin-4-amine (1.0 eq), (2-formylphenyl)boronic acid (1.5 eq) and Na$_2$CO$_3$ (2M aqueous solution, 3 eq) in dioxane and the resulting mixture was heated at 100° C. for 1 h. The solution was allowed to cool to RT and then filtered through a pad of celite. The filter cake was washed with MeOH and the filtrate was concentrated under reduced pressure. The dark residue obtained was dissolved in a 1/1 v/v mixture of tent-butanol and 2-methyl-2-butene, a solution of NaClO$_2$ (10 eq) and KH$_2$PO$_4$ (7.5 eq) in water was added and the reaction mixture was stirred at RT for 8 h. Volatiles were removed under reduced pressure and the residue was purified by preparative RP-HPLC eluting with MeCN/water containing 0.1% TFA to give the title compound. $^1$H NMR (400 MHz, DMSO-d$_6$) δ 11.00 (s, 1H), 8.52 (s, 1H), 8.42 (s, 1H), 8.35 (d, J 7.8, 1H), 7.87 (d, J 7.8, 1H), 7.60 (m, 1H), 7.34 (m, 1H), 6.22 (s, 1H), 4.11 (m, 1H), 4.00-3.89 (m, 2H), 3.78 (m, 1H), 0.79 (s, 3H); MS (ES$^+$) C$_{19}$H$_{18}$N$_4$O$_5$ requires: 382, found: 383 (M+H$^+$).

Example 2

Entry 2, Table A 2-(2-C-methyl-β-D-ribofuranosyl)-6,7-dihydro-2H-2,3,5,6-tetraazadibenzo[cd,h]azulene

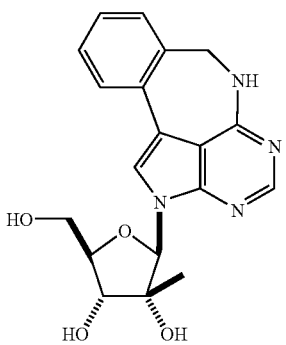

Pd(Ph$_3$P)$_4$ (0.1 eq) was added to a solution of 5-iodo-7-(2-C-methyl-β-D-ribofuranosyl)-7H-pyrrolo[2,3-c/]pyrimidin-4-amine (1.0 eq), (2-formylphenyl)boronic acid (1.5 eq) and sodium carbonate (2M aqueous solution, 3 eq) in dioxane and the resulting mixture was heated at 100° C. for 1 h. The solution was allowed to cool to RT and then filtered through a pad of celite. The filter cake was washed with MeOH and the filtrate was concentrated under reduced pressure. The dark residue obtained was dissolved in MeCN, acetic acid (0.5 eq) was added followed by molecular sieves. The resulting suspension was stirred for 5 min, NaBH$_3$CN (1.2 eq) was then added and the reaction mixture was stirred at RT for 12 h. The reaction was quenched with 1M aq. NaOH, the volatiles were removed under reduced pressure and the residue was purified by preparative RP-HPLC eluting with MeCN/water containing 0.1% TFA to give the title compound. $^1$H NMR (400 MHz, D$_2$O) δ 8.28 (s, 1H), 8.12 (s, 1H), 7.67 (m, 1H), 7.50 (m, 1H), 7.42-7.36 (m, 2H), 6.39 (s, 1H), 4.57 (d, J 5.2, 2H), 4.28-4.16 (m, 3H), 4.05 (m, 1H), 0.98 (s, 3H); MS (ES$^+$) C$_{19}$H$_{20}$N$_4$O$_4$ requires: 368, found: 369 (M+H$^+$).

Example 3

Entry 3, Table A and Entry 4, Table A 2-(2-C-methyl-β-D-ribofuranosyl)-2,6-dihydro-7H-8-thia-2,3,5,6-tetraazabenzo[CD]cyclopenta[H]azulen-7-one and 2-(2-C-methyl-β-D-ribofuranosyl)-6,7-dihydro-2H-8-thia-2,3,5,6-tetraazabenzo[CD]cyclopenta[H]azulene

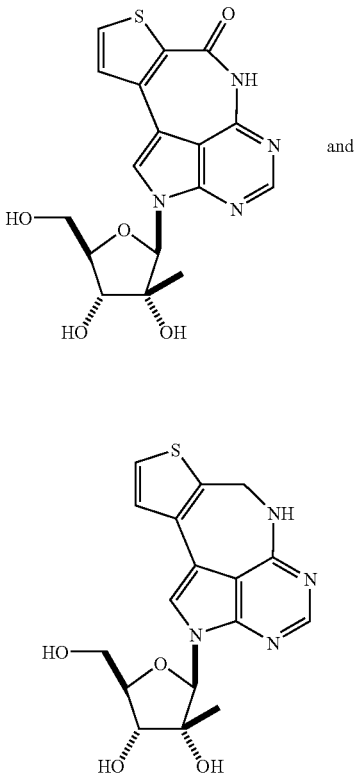

and

Pd(Ph₃P)₄ (0.1 eq) was added to a solution of 5-iodo-7-(2-C-methyl-β-D-ribofuranosyl)-7H-pyrrolo[2,3-c/]pyrimidin-4-amine (1.0 eq), (2-formylphenyl)boronic acid (1.5 eq) and sodium carbonate (2M aqueous solution, 3 eq) in dioxane and the resulting mixture was heated at 100° C. for 1 h. The solution was allowed to cool to RT and then filtered through a pad of celite. The filter cake was washed with methanol and the filtrate was concentrated under reduced pressure. The dark residue obtained was purified by preparative RP-HPLC eluting with MeCN/water containing 0.1% TFA to give 2-(2-C-methyl-β-D-ribofuranosyl)-2,6-dihydro-7H-8-thia-2,3,5,6-tetraazabenzo[CD]cyclopenta[H]azulen-7-one as first eluting product and 2-(2-C-methyl-(3-D-ribofuranosyl)-6,7-dihydro-2H-8-thia-2,3,5,6-tetraazabenzo[CD]cyclopenta[H]azulene as second eluting product.

2-(2-C-methyl-β-D-ribofuranosyl)-2,6-dihydro-7H-8-thia-2,3,5,6-tetraazabenzo[CD]cyclopenta[H]azulen-7-one: ¹H NMR (600 MHz, DMSO-d₆) δ 11.07 (s, 1H), 8.39 (s, 1H), 8.20 (s, 1H), 8.02 (d, J 4.6, 1H), 7.74 (d, J 4.6, 1H), 6.19 (s, 1H), 5.31-5.16 (m, 3H), 4.02 (m, 1H), 3.94 (m, 1H), 3.89 (m, 1H), 3.76 (m, 1H) 0.79 (s, 3H); MS (ES⁺) C₁₇H₁₆N₄O₅S requires: 388, found: 389 (M+H⁺).

2-(2-C-methyl-β-D-ribofuranosyl)-6,7-dihydro-2H-8-thia-2,3,5,6-tetraazabenzo[CD]cyclopenta[H]azulene: ¹H NMR (600 MHz, D₂O/CD₃CN) δ 8.24 (s, 1H), 7.96 (s, 1H), 7.37 (d, J 5.3, 1H), 7.30 (d, J 5.3, 1H), 6.26 (s, 1H), 4.69 (s, 2H), 4.10 (d, J 8.8, 1H), 4.03-3.96 (m, 2H), 3.85-3.82 (m, 1H), 0.86 (s, 3H). MS (ES) C₁₇H₁₈N₄O₄S requires: 374, found: 375 (M+H⁺).

Example 4

Entry 5, Table A

2-[5-O-(hydroxy{[hydroxy(phosphonooxy)phosphoryl]oxy}phosphoryl)-2-C-methyl-β-D-ribofuranosyl]-2,6-dihydro-7H-2,3,5,6-tetraazadibenzo[cd,h]azulen-7-one

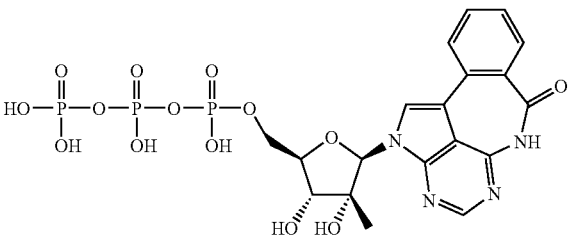

Neat POCl₃ (2.5 eq) was added via a syringe to a 0.1 M solution of 2-(2-c-methyl-beta-d-ribofuranosyl)-2,6-dihydro-7h-2,3,5,6-tetraazadibenzo[cd,h]azulen-7-one in dry trimethyl phosphate at 0° C. After stirring for 2 h at 0° C. a mixture of bis tributylammonium pyrophosphate (0.5 M in dry DMF, 6.0 eq) and tributylamine (5.0 eq) was quickly added to the reaction mixture under vigorous stirring. After 1 min at 0° C., 1 M aq. triethylammonium hydrogenocarbonate (100 eq) was poured into the solution. The reaction mixture was stirred 3 h at RT and conconcentrated under reduced pressure (cold bath). The residue was dissolved in water and purified by RP-HPLC (mobile phase: dimethylhexylammonium bicarbonate/MeCN) to afford the title compound in 30% yield as a tris dimethylhexylammonium salt (colourless oil). ¹H NMR (300 MHz, D₂O, 300 K) δ 8.34 (s, 1H), 8.16 (d, J 8.4, 1H), 8.06-7.99 (m, 2H), 7.64 (m, 1H), 7.33 (m, 1H), 6.31 (s, 1H), 4.59 (m, 1H), 4.48 (m, 1H), 4.41-4.29 (m, 2H), 3.21-3.06 (m, 6H), 2.90 (bs, 18H), 1.79-1.64 (m, 6H), 1.42-1.25 (m, 18H), 0.94-0.83 (m, 12H). ³¹P NMR (300 MHz, D₂O, 300 K) δ-23.09 (bt, J 20.4, 19.6, 1P), −11.21 (d, J 20.4, 1P), 10.76 (d, J 19.6, 1P). MS (ES⁻) m/z 621 (M−H)⁻

The following table lists specific compounds of the present invention. The table provides the structure and name of each compound and the observed mass as determined via ES-MS either as its molecular ion plus H (M+1) or its molecular ion minus H (M−1) for positive and negative ionisation mode respectively. The synthetic scheme employed to prepare the compound is indicated in the last column.

TABLE A

| Entry | Structure | Name | parent weight | observed mass | Scheme |
|---|---|---|---|---|---|
| 1 | 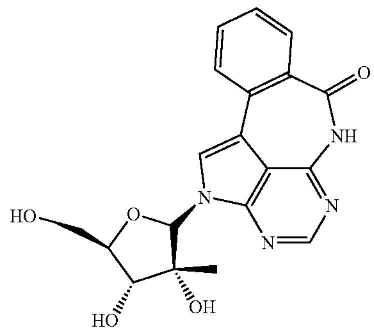 | 2-(2-C-methyl-beta-D-ribofuranosyl)-2,6-dihydro-7H-2,3,5,6-tetraazadibenzo[C,D,H]azulen-7-one | 382.1 | 383 (M + 1) | 1 |
| 2 | 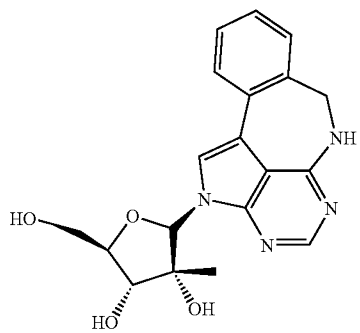 | 2-(2-C-methyl-beta-D-ribofuranosyl)-6,7-dihydro-2H-2,3,5,6-tetraazadibenzo[cd,h]azulene | 368.1 | 369 (M + 1) | 2 |
| 3 | 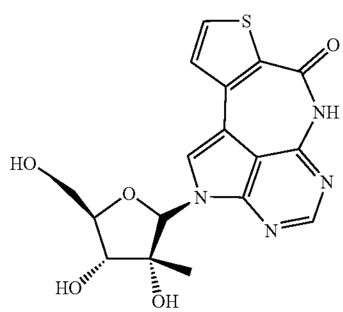 | 2-(2-C-methyl-beta-D-ribofuranosyl)-2,6-dihydro-7H-8-thia-2,3,5,6-tetraazabenzo[CD]cyclopenta[H]azulen-7-one | 388.4 | 389 (M + 1) | 3 |
| 4 | 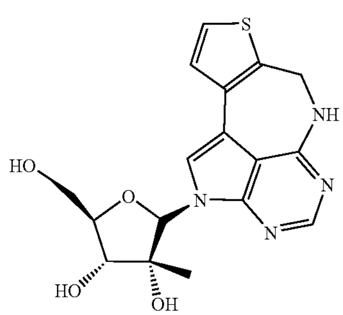 | 2-(2-C-methyl-beta-D-ribofuranosyl)-6,7-dihydro-2H-8-thia-2,3,5,6-tetraazabenzo[CD]cyclopenta[H]azulene | 374.4 | 375 (M + 1) | 3 |
| 5 | 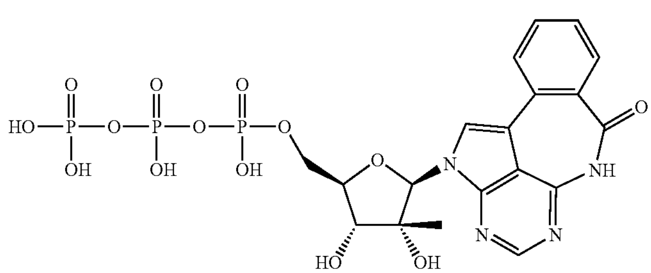 | 2-[5-O-(hydroxy{[hydroxy(phosphonooxy)phosphoryl]oxy}phosphoryl)-2-C-methyl-beta-D-ribofuranosyl]-2,6-dihydro-7H-2,3,5,6-tetraazadibenzo[cd,h]azulen-7-one | 622 | 621 (M − H) | 4 |

TABLE A-continued

| Entry | Structure | Name | parent weight | observed mass | Scheme |
|---|---|---|---|---|---|
| 6 | 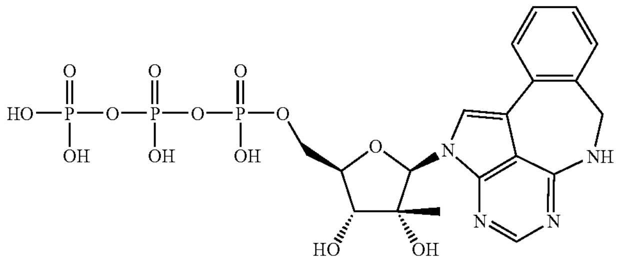 | 2-[5-O-(hydroxy{[hydroxy(phosphono-oxy)phosphoryl]oxy}phosphoryl)-2-C-methyl-beta-D-ribofuranosyl]-6,7-dihydro-2H-2,3,5,6-tetraazadibenzo[cd,h]azulene | 608 | 607 (M − H) | 4 |
| 7 | 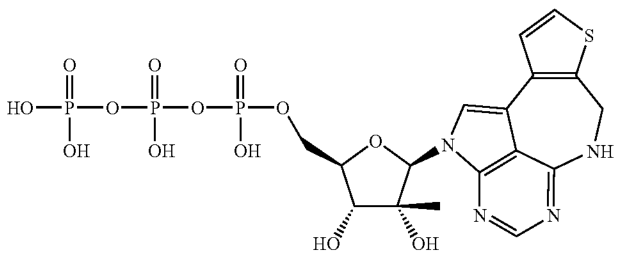 | 2-[5-O-(hydroxy{[hydroxy(phosphono-oxy)phosphoryl]oxy}phosphoryl)-2-C-methyl-beta-D-ribofuranosyl]-6,7-dihydro-2H-8-thia-2,3,5,6-tetraazabenzo[cd]cyclopenta[h]azulene | 614 | 613 (M − H) | 4 |
| 8 | 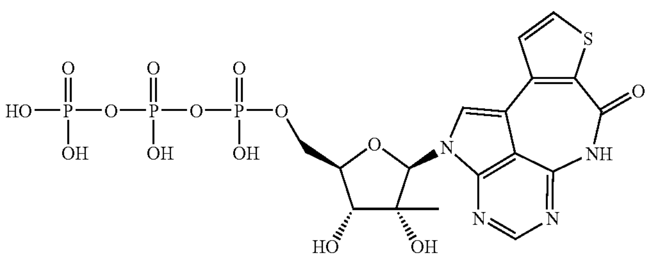 | 2-[5-O-(hydroxy{[hydroxy(phosphono-oxy)phosphoryl]oxy}phosphoryl)-2-C-methyl-beta-D-ribofuranosyl]-2,6-dihydro-7H-8-thia-2,3,5,6-tetraazabenzo[cd]cyclopenta[h]azulen-7-one | 628 | 627 (M − H) | 4 |

Biogical Assays

The assays employed to measure the inhibition of HCV NS5B polymerase and HCV replication are described below.

The effectiveness of the compounds of the present invention as inhibitors of HCV NS5B RNA-dependent RNA polymerase (RdRp) was measured in the following assay.

A. Assay for Inhibition of HCV NS5B Polymerase:

This assay was used to measure the ability of the nucleoside derivatives of the present invention to inhibit the enzymatic activity of the RNA-dependent RNA polymerase (NS5B) of the hepatitis C virus (HCV) on a heteromeric RNA template.

Procedure:
Assay Buffer Conditions: (52.5 μL-total/reaction)
20 mM Tris, pH 7.5
45 mM KCl
2 mM MgCl2
0.01% Triton X-100
1 μg BSA, DNase Free
1 mM DTT
2 nM DC55-1b.BK or 10 nM DC55-2b.2
20 nM heterogeneous template dCoh
UTP 1 uM
ATP 1 uM
CTP 1 uM
GTP 1 uM
3H-UTP 1,000,000 cpm
2.5 μl reaction inhibitor compound in H$_2$O The compounds were tested at various concentrations up to 100 μM final concentration. Nucleoside derivatives were pipetted into wells of a 96-well plate. The enzyme diluted in the reaction buffer was pipetted into the wells and incubated at room temperature for 10 minutes; then the template dCoh was added and incubated for 10 minutes at room temperature. The reaction was initiated by addition of a mixture of nucleotide triphosphates (NTP's), including the radiolabeled UTP, and allowed to proceed at room temperature for 2 hours. Blank samples were done omitting the dCoh template. The reaction was quenched by addition of 50 ul TCA 20% (trichloroacetic acid)/NaPPi 20 mM and the plates were put in ice for 5 minutes. Then, the mixtures were filtered onto Unifilter GF/B 96-well plates (PerkinElmer), washed with TCA 2.5%. P 50 ul/well of scintillator solution (Microscint 20, PerkinElmer) were added and the plates were counted in a scintillator counter.

The percentage of inhibition was calculated according to the following equation:

% Inhibition=[1−(*cpm* in test reaction−*cpm* in blank)/ (*cpm* in control reaction−*cpm* in blank)]×100.

Representative compounds were tested in the HCV NS5B polymerase assay and results are reported as IC50 activity ranges in Table B

TABLE B

| Compound | Structure | IC$_{50}$ (μM) |
|---|---|---|
| 5 | (structure) | +++ |
| 6 | (structure) | ++ |
| 7 | (structure) | ++ |
| 8 | (structure) | +++ |

Activity ranges:
+++: < 1μM; ++: 1-30 μM; +: > 30 μM;

B. Assay for Inhibition of HCV RNA Replication:

The compounds of the present invention were also evaluated for their ability to affect the replication of Hepatitis C Virus RNA in cultured hepatoma (HuH-7) cells containing a subgenomic HCV Replicon. The details of the assay are described below. This Replicon assay is a modification of that described in V. Lohmann, F. Korner, J-O. Koch, U. Herian, L. Theilmann, and R. Bartenschlager, "Replication of a Subgenomic Hepatitis C Virus RNAs in a Hepatoma Cell Line," Science 285:110 (1999).

Protocol:

The assay was an in situ Ribonuclease protection, Scintillation Proximity based-plate assay (SPA). 10,000-40,000 cells were plated in 100-200 μL of media containing 0.8 mg/mL G418 in 96-well cytostar plates (Amersham). Compounds were added to cells at various concentrations up to 100 μM in 1% DMSO at time 0 to 18 h and then cultured for 24-96 h. Cells were fixed (20 min, 10% formalin), permeabilized (20 min, 0.25% Triton X-100/PBS) and hybridized (overnight, 50° C.) with a single-stranded $^{33}$P RNA probe complementary to the (+) strand NS5B (or other genes) contained in the RNA viral genome. Cells were washed, treated with RNAse, washed, heated to 65° C. and counted in a Top-Count Inhibition of replication was read as a decrease in counts per minute (cpm).

Human HuH-7 hepatoma cells, which were selected to contain a subgenomic replicon, carry a cytoplasmic RNA consisting of an HCV 5' non-translated region (NTR), a neomycin selectable marker, an EMCV IRES (internal ribosome entry site), and HCV non-structural proteins NS3 through NS5B, followed by the 3' NTR.

Representative compounds were tested in the HCV replication assay and results are reported as EC50 activity ranges in Table C

TABLE C

| Compound | Structure | EC$_{50}$ (μM) |
|---|---|---|
| 1 | (structure) | +++ |
| 2 | (structure) | ++ |
| 3 | (structure) | +++ |
| 4 | (structure) | +++ |

Activity ranges:
+++: <30 μM; ++: 30-50 μM; +: >50 μM;

The nucleoside derivatives of the present invention were also evaluated for cellular toxicity and anti-viral specificity in the counterscreens described below.

C. Counterscreens:

The ability of the nucleoside derivatives of the present invention to inhibit human DNA polymerases was measured in the following assays.

a. Inhibition of Human DNA Polymerases Alpha and Beta:

Reaction Conditions:

50 μL at reaction volume

Reaction Buffer Components:
20 mM Tris-HCl, pH 7.5
200 μg/mL bovine serum albumin
100 mM KCl
2 mM β-mercaptoethanol
10 mM MgCl$_2$
1.6 μM dA, dG, dC, dTTP
α-$^{33}$P-dATP Enzyme and Template:
0.05 mg/mL gapped fish sperm DNA template
0.01 U/μLK at DNA polymerase α or β

Preparation of Gapped Fish Sperm DNA Template:
Add 5 μL 1M MgCl$_2$ to 500 μL activated fish sperm DNA (USB 70076);
Warm to 37° C. and add 30 μL of 65 U/μL of exonuclease III (GibcoBRL 18013-011);
Incubate 5 min at 37° C.;
Terminate reaction by heating to 65° C. for 10 min;
Load 50-100 μL aliquots onto Bio-spin 6 chromatography columns (Bio-Rad 732-6002) equilibrated with 20 mM Tris-HCl, pH 7.5;
Elute by centrifugation at 1,000×g for 4 min;
Pool eluate and measure absorbance at 260 nm to determine concentration.

The DNA template was diluted into an appropriate volume of 20 mM Tris-HCl, pH 7.5 and the enzyme was diluted into an appropriate volume of 20 mM Tris-HCl, containing 2 mM β-mercaptoethanol, and 100 mM KCl. Template and enzyme were pipetted into microcentrifuge tubes or a 96 well plate. Blank reactions excluding enzyme and control reactions excluding test compound were also prepared using enzyme dilution buffer and test compound solvent, respectively. The reaction was initiated with reaction buffer with components as listed above. The reaction was incubated for 1 hour at 37° C. The reaction was quenched by the addition of 20 μL 0.5M EDTA. 50 μL of the quenched reaction was spotted onto Whatman DE81 filter disks and air dried. The filter disks were repeatedly washed with 150 mL 0.3M ammonium formate, pH 8 until 1 mL of wash is <100 cpm. The disks were washed twice with 150 mL absolute ethanol and once with 150 mL anhydrous ether, dried and counted in 5 mL scintillation fluid.

The percentage of inhibition was calculated according to the following equation: % inhibition=[1−(cpm in test reaction−cpm in blank)/(cpm in control reaction−cpm in blank)]×100.

b. Inhibition of Human DNA Polymerase Gamma:

The potential for inhibition of human DNA polymerase gamma was measured in reactions that included 0.5 ng/μL enzyme; 10 μM dATP, dGTP, dCTP, and TTP; 2 μCi/reaction [α-$^{33}$P]-dATP, and 0.4 μg/μL activated fish sperm DNA (purchased from US Biochemical) in a buffer containing 20 mM Tris pH8, 2 mM (3-mercaptoethanol, 50 mM KCl, 10 mM MgCl$_2$, and 0.1 μg/μL BSA. Reactions were allowed to proceed for 1 h at 37° C. and were quenched by addition of 0.5 M EDTA to a final concentration of 142 mM. Product formation was quantified by anion exchange filter binding and scintillation counting. Compounds were tested at up to 50 μM.

The percentage of inhibition was calculated according to the following equation: % inhibition=[1−(cpm in test reaction−cpm in blank)/(cpm in control reaction−cpm in blank)]×100.

The ability of the nucleoside derivatives of the present invention to inhibit HIV infectivity and HIV spread was measured in the following assays.

c. HIV Infectivity Assay

Assays were performed with a variant of HeLa Magi cells expressing both CXCR4 and CCR5 selected for low background β-galactosidase ((β-gal) expression. Cells were infected for 48 h, and β-gal production from the integrated HIV-1 LTR promoter was quantified with a chemiluminescent substrate (Galactolight Plus, Tropix, Bedford, Mass.) Inhibitors were titrated (in duplicate) in twofold serial dilutions starting at 100 μM; percent inhibition at each concentration was calculated in relation to the control infection.

d. Inhibition of HIV Spread

The ability of the compounds of the present invention to inhibit the spread of the human immunedeficiency virus (HIV) was measured by the method described in U.S. Pat. No. 5,413,999 (May 9, 1995), and J. P. Vacca, et al., *Proc. Natl. Acad. Sci.*, 91: 4096-4100 (1994), which are incorporated by reference herein in their entirety.

The nucleoside derivatives of the present invention were also screened for cytotoxicity against cultured hepatoma (HuH-7) cells containing a subgenomic HCV Replicon in an MTS cell-based assay as described in the assay below. The HuH-7 cell line is described in H. Nakabayashi, et al., *Cancer Res.*, 42: 3858 (1982).

e. Cytotoxicity Assay:

Cell cultures were prepared in appropriate media at concentrations of approximately $1.5 \times 10^5$ cells/mL for suspension cultures in 3 day incubations and $5.0 \times 10^4$ cells/mL for adherent cultures in 3 day incubations. 99 μL, of cell culture was transferred to wells of a 96-well tissue culture treated plate, and 1 μL, of 100-times final concentration of the test compound in DMSO was added. The plates were incubated at 37° C. and 5% $CO_2$ for a specified period of time. After the incubation period, 20 μL, of CellTiter 96 Aqueous One Solution Cell Proliferation Assay reagent (MTS) (Promega) was added to each well and the plates were incubated at 37° C. and 5% $CO_2$ for an additional period of time up to 3 h. The plates were agitated to mix well and absorbance at 490 nm was read using a plate reader. A standard curve of suspension culture cells was prepared with known cell numbers just prior to the addition of MTS reagent. Metabolically active cells reduce MTS to formazan. Formazan absorbs at 490 nm. The absorbance at 490 nm in the presence of compound was compared to absorbance in cells without any compound added. Reference: Cory, A. H. et al., "Use of an aqueous soluble tetrazolium/formazan assay for cell growth assays in culture," *Cancer Commun.* 3: 207 (1991).

The following assays were employed to measure the activity of the compounds of the present invention against other RNA-dependent RNA viruses:

a. Determination of In Vitro Antiviral Activity of Compounds Against Rhinovirus (Cytopathic Effect Inhibition Assay):

Assay conditions are described in the article by Sidwell and Huffman, "Use of disposable microtissue culture plates for antiviral and interferon induction studies," *Appl. Microbiol.* 22: 797-801 (1971).

Viruses:

Rhinovirus type 2 (RV-2), strain HGP, was used with KB cells and media (0.1% $NaHCO_3$, no antibiotics) as stated in the Sidwell and Huffman reference. The virus, obtained from the ATCC, was from a throat swab of an adult male with a mild acute febrile upper respiratory illness. Rhinovirus type 9 (RV-9), strain 211, and rhinovirus type 14 (RV-14), strain Tow, were also obtained from the American Type Culture Collection (ATCC) in Rockville, Md. RV-9 was from human throat washings and RV-14 was from a throat swab of a young adult with upper respiratory illness. Both of these viruses were used with HeLa Ohio-1 cells (Dr. Fred Hayden, Univ. of VA) which were human cervical epitheloid carcinoma cells.

MEM (Eagle's minimum essential medium) with 5% Fetal Bovine serum (FBS) and 0.1% $NaHCO_3$ was used as the growth medium.

Antiviral test medium for all three virus types was MEM with 5% FBS, 0.1% $NaHCO_3$, 50 μg gentamicin/mL, and 10 mM $MgCl_2$.

2000 μg/mL was the highest concentration used to assay the compounds of the present invention.

Virus was added to the assay plate approximately 5 min after the test compound. Proper controls were also run. Assay plates were incubated with humidified air and 5% $CO_2$ at 37° C. Cytotoxicity was monitored in the control cells microscopically for morphologic changes. Regression analysis of the virus CPE data and the toxicity control data gave the ED50 (50% effective dose) and CC50 (50% cytotoxic concentration). The selectivity index (SI) was calculated by the formula: SI=CC50÷ED50.

b. Determination of In Vitro Antiviral Activity of Compounds Against Dengue, Banzi, and Yellow Fever (CPE Inhibition Assay)

Assay details are provided in the Sidwell and Huffman reference above.

Viruses:

Dengue virus type 2, New Guinea strain, was obtained from the Center for Disease Control. Two lines of African green monkey kidney cells were used to culture the virus (Vero) and to perform antiviral testing (MA-104). Both Yellow fever virus, 17D strain, prepared from infected mouse brain, and Banzi virus, H 336 strain, isolated from the serum of a febrile boy in South Africa, were obtained from ATCC. Vero cells were used with both of these viruses and for assay.

Cells and Media:

MA-104 cells (BioWhittaker, Inc., Walkersville, Md.) and Vero cells (ATCC) were used in Medium 199 with 5% FBS and 0.1% $NaHCO_3$ and without antibiotics. Assay medium for dengue, yellow fever, and Banzi viruses was MEM, 2% FBS, 0.18% $NaHCO_3$ and 50 μg gentamicin/mL.

Antiviral testing of the compounds of the present invention was performed according to the Sidwell and Huffman reference and similar to the above rhinovirus antiviral testing. Adequate cytopathic effect (CPE) readings were achieved after 5-6 days for each of these viruses.

c. Determination of In Vitro Antiviral Activity of Compounds Against West Nile Virus (CPE Inhibition Assay)

Assay details are provided in the Sidwell and Huffman reference cited above. West Nile virus, New York isolate derived from crow brain, was obtained from the Center for Disease Control. Vero cells were grown and used as described above. Test medium was MEM, 1% FBS, 0.1% $NaHCO_3$ and 50 μg gentamicin/mL.

Antiviral testing of the compounds of the present invention was performed following the methods of Sidwell and Huffman which are similar to those used to assay for rhinovirus activity. Adequate cytopathic effect (CPE) readings were achieved after 5-6 days.

d. Determination of In Vitro Antiviral Activity of Compounds Against rhino, yellow fever, dengue, Banzi, and West Nile Viruses (Neutral Red Uptake Assay)

After performing the CPE inhibition assays above, an additional cytopathic detection method was used which is described in "Microtiter Assay for Interferon: Microspectrophotometric Quantitation of Cytopathic Effect," *Appl. Environ. Microbiol.* 31: 35-38 (1976). A Model EL309 microplate reader (Bio-Tek Instruments Inc.) was used to read the assay plate. ED50's and CD50's were calculated as above.

Example of a Pharmaceutical Formulation

As a specific embodiment of an oral composition of a compound of the present invention, 50 mg of any one of Examples 1 to 4 is formulated with sufficient finely divided lactose to provide a total amount of 580 to 590 mg to fill a size 0 hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

The invention claimed is:

1. A compound of structural formula (I):

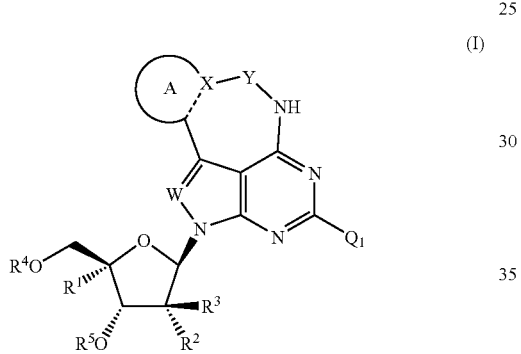

or a pharmaceutically acceptable salt thereof; wherein
ring A is a 5- or 6-membered ring, optionally containing 1, 2 or 3 heteroatoms selected from N, O and S, and optionally containing one, two or three double bonds, and also optionally substituted by 1, 2 or 3 groups independently selected from CN, $C_{1-6}$alkyl, $C_{2-6}$alkenyl, $C_{2-6}$ alkynyl, $C_{1-6}$alkoxy, halogen, $C_{1-6}$haloalkyl, $C_{1-6}$haloalkoxy, $NR^xR^y$, $NR^zC(O)NR^xR^y$, $NR^xC(O)OR^y$, $OC(O)NR^xR^y$, $C(O)R^x$, $C(O)OR^x$, $C(O)NR^xR^y$, $SR^x$, $S(O)R^x$, $SO_2R^x$, $SO_2NR^xR^y$, wherein $R^x$, $R^y$ and $R^z$ are independently selected from hydrogen and $C_{1-6}$alkyl; and further optionally fused to another 5- or 6-membered ring, which ring optionally contains 1, 2 or 3 heteroatoms selected from N, O and S, and which ring optionally contains 1, 2 or 3 double bonds, and which ring is optionally substituted by 1, 2 or 3 groups independently selected from $C_{1-6}$alkyl, $C_{1-6}$alkoxy and halogen;
$Q^1$ is hydrogen or amino;
W is CH or amino;
X is CH, C or N;
the dotted bond represents a single bond when X is CH or N, or the dotted bond represents a double bond when X is C;
Y is C=O or $CH_2$;
$R^1$ is hydrogen, methyl, hydroxymethyl, fluoromethyl or $N_3$;
$R^2$ and $R^3$ are independently hydrogen, fluorine, hydroxy, $C_{1-4}$alkyl or $C_{1-4}$alkoxy;
$R^4$ is hydrogen, $PO_3H_2$, $P_2O_6H_3$, $P_3O_9H_4$ or a group $R^6$ wherein $R^6$ is $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl or a monophosphate prodrug residue of the formula

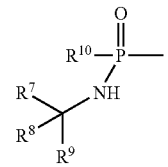

wherein $R^7$ is hydrogen, $C_{1-6}$alkyl optionally substituted with one substituent selected from the group consisting of fluoro, hydroxy, methoxy, amino, carboxy, carbamoyl, guanidino, mercapto, methylthio, 1H-imidazolyl, and 1H-indol-3-yl; or $R^7$ is phenyl, benzyl or phenethyl each optionally substituted with one to two substituents independently selected from the group consisting of halogen, hydroxy, and methoxy;
$R^8$ is hydrogen or methyl;
or $R^7$ and $R^8$ together with the carbon atom to which they attached form a 3- to 6-membered aliphatic spirocyclic ring system;
$R^9$ is aryl, arylalkyl, heteroaryl or

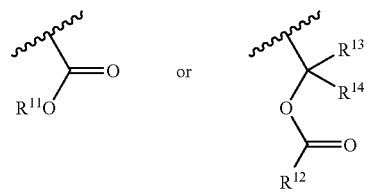

wherein $R^{11}$ is $C_{1-16}$alkyl, $C_{2-20}$alkenyl, $(CH_2)_{0-4}C_{7-9}$cycloalkyl, $(CH_2)_{0-4}C_{3-9}$cycloalkenyl or adamantly each optionally substituted with one to three substituents independently selected from halogen, hydroxy, carboxy, $C_{1-4}$alkoxy, trifluoromethyl and $(CH_2)_{0-4}NR^{15}R^{16}$ wherein $R^{15}$ and $R^{16}$ are independently selected from hydrogen and $C_{1-6}$alkyl; or $R^{15}$ and $R^{16}$, together with the nitrogen atom to which they are attached form a 4- to 7-membered heterocyclic ring optionally containing 1 or 2 more heteroatoms selected from N, O and S, which ring is optionally substituted by $C_{1-6}$ alkyl;
$R^{10}$ is hydroxy or a group $OR^{16}$ wherein $R^{16}$ is $CH_2OC(O)$ $R^{17}$ or $CH_2CH_2SR^{17}$ where $R^{17}$ is $C_{1-6}$ alkylcarbonyl optionally substituted by a hydroxyl group or $R^{16}$ is $(CH_2)_{2-4}-O-(CH_2)_{1-17}CH_3$, or an aromatic ring selected from phenyl, naphthyl, pyridinyl, pyrimidinyl, pyrazinyl, pyridazinyl, indolyl, quinolinyl, or isoquinolinyl, wherein the aromatic ring is optionally substituted with one to five substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl; or $R^{10}$ and $R^5$ form a bond to make a cyclic phosphate group;
$R^{12}$ is $C_{6-16}$alkyl, $C_{2-20}$alkenyl, $(CH_2)_{0-2}C_{7-9}$cycloalkyl, $(CH_2)_{0-2}C_{3-9}$cycloalkenyl, $OC_{1-6}$alkyl or adamantyl; and $R^{13}$ and $R^{14}$ are independently selected from hydrogen and $C_{1-6}$alkyl;

or $R^{13}$ and $R^{14}$ together with the carbon atom to which they attached form a 3- to 6-membered aliphatic spirocyclic ring system;

$R^5$ is hydrogen or methyl, $C_{1-16}$ alkylcarbonyl, $C_{2-18}$ alkenylcarbonyl, $C_{1-10}$alkyloxycarbonyl, $C_{3-6}$ cycloalkylcarbonyl, $C_{3-6}$ cycloalkyloxycarbonyl or an amino acyl residue of structural formula:

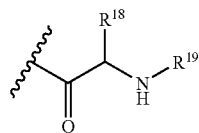

wherein $R^{18}$ is hydrogen, $C_{1-5}$ alkyl or phenyl$C_{0-2}$ alkyl; and $R^{19}$ is hydrogen, $C_{1-4}$ alkyl, $C_{1-4}$ alkylsulfonyl or phenyl$C_{0-2}$ alkylsulfonyl, or a group $COR^{20}$ wherein $R^{20}$ is $C_{1-4}$ alkyl optionally substituted by phenyl, $C_{1-4}$ alkoxy optionally substituted by phenyl, or $C_{1-4}$alkylamino optionally substituted by $C_{1-4}$ alkyl optionally substituted by phenyl.

2. A compound of structural formula (Ia):

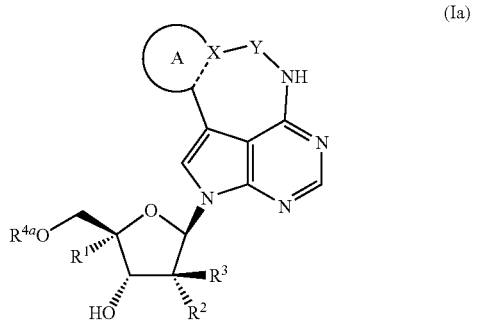

(Ia)

or a pharmaceutically acceptable salt thereof; wherein:

ring A is a 5- or 6-membered ring, optionally containing 1, 2 or 3 heteroatoms selected from N, O and S, and optionally containing one, two or three double bonds, and also optionally substituted by 1, 2 or 3 groups independently selected from CN, $C_{1-6}$alkyl, $C_{2-6}$alkenyl, $C_{2-6}$ alkynyl, $C_{1-6}$alkoxy, halogen, $C_{1-6}$haloalkyl, $C_{1-6}$haloalkoxy, $NR^xR^y$, $NR^zC(O)NR^xR^y$, $NR^xC(O)OR^y$, $OC(O)NR^xR^y$, $C(O)R^x$, $C(O)OR^x$, $C(O)NR^xR^y$, $SR^x$, $S(O)R^x$, $SO_2R^x$, $SO_2NR^xR^y$, wherein $R^x$, $R^y$ and $R^z$ are independently selected from hydrogen and $C_{1-6}$alkyl; and further optionally fused to another 5- or 6-membered ring, which ring optionally contains 1, 2 or 3 heteroatoms selected from N, O and S, and which ring optionally contains 1, 2 or 3 double bonds, and which ring is optionally substituted by 1, 2 or 3 groups independently selected from $C_{1-6}$alkyl, $C_{1-6}$alkoxy and halogen;

X is CH, C or N;

the dotted bond represents a single bond when X is CH or N, or the dotted bond represents a double bond when X is C;

Y is C=O or $CH_2$;

$R^1$ is hydrogen, methyl, hydroxymethyl, fluoromethyl or $N_3$;

$R^2$ and $R^3$ are independently hydrogen, fluorine, hydroxy, $C_{1-4}$alkyl or $C_{1-4}$alkoxy;

$R^{4a}$ is hydrogen, $C(O)C_{1-10}$alkyl, $PO_3H_2$, $P_2O_6H_3$, $P_3O_9H_4$ or $P(O)R^aR^b$; wherein $R^a$ and $R^b$ are each independently hydroxy, OAr, $OCH_2CH_2SC(=O)C_{1-4}$alkyl, $OCH_2CH_2SC(=O)C_{1-4}$ hydroxyalkyl, $OCH_2O(C=O)OC_{1-4}$alkyl, $NHCR^cR^dCO_2R^e$, $NR^cR^d$,$OCH(C_{1-4}$alkyl)$O(C=O)$ $C_{1-4}$ alkyl,

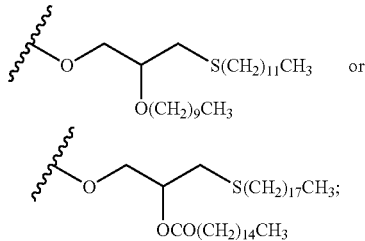

Ar is phenyl, naphythyl, pyridinyl, pyrimidinyl, pyrazinyl, pyridazinyl, indolyl, quinolinyl or isoquinolinyl, wherein Ar is optionally substituted with one to five substituents independently selected from the group consisting of halogen, $C_{1-4}$alkyl, $C_{1-4}$alkoxy, $C_{1-4}$alkylthio, cyano, nitro, amino, carboxy, trifluoromethyl, trifluoromethoxy, $C_{1-4}$alkylamino, di($C_{1-4}$alkyl)amino, $C_{1-4}$alkylacarbonyl, $C_{1-4}$alkylcarbonyloxy and $C_{1-4}$alkyloxycarbonyl;

$R^c$ is hydrogen, $C_{1-6}$alkyl, phenyl or benzyl, wherein alkyl is optionally substituted with one substituent selected from fluorine, hydroxy, methoxy, amino, carboxy, carbamoyl, guanidino, mercapto, methylthio, 1H-imidazolyl, and 1H-indol-3-yl, and wherein phenyl and benzyl are optionally substituted with one or two substituents independently selected from halogen, hydroxy or methoxy;

$R^d$ is hydrogen or methyl;

or $R^c$ and $R^d$ together with the carbon atom to which they are attached fern form a 3- to 6-membered aliphatic spirocyclic ring system;

$R^e$ is hydrogen, $C_{1-16}$alkyl, $C_{2-20}$alkenyl, $(CH_2)_{0-2}C_{3-6}$cycloalkyl, phenyl, benzyl or adamantyl; wherein alkyl, alkenyl, cycloalkyl and adamantyl are optionally substituted with one to three substituents independently selected from halogen, hydroxy, carboxy, $C_{1-4}$alkoxy; and wherein phenyl and benzyl are optionally substituted with one to three substituents independently selected from halogen, hydroxy, cyano, $C_{1-4}$alkoxy, trifluoromethyl and trifluoromethoxy.

3. A compound according to either claim 1 or claim 2 in which A is a 5- or 6-membered ring, optionally containing one heteroatom selected from N, O and S, and optionally containing two or three double bonds.

4. A compound according to claim 1 in which X is C and the dotted bond represents a double bond or X is N and the dotted bond represents a single bond.

5. A compound according to claim 1 in which $R^1$ is hydrogen.

6. A compound according to claim 1 in which $R^2$ is hydroxyl.

7. A compound according to claim 1 in which $R^3$ is methyl.

8. A compound according to claim 1 in which $R^4$ or $R^{4a}$ is hydrogen, $C(O)C_{1-10}$alkyl, $PO_3H_2$, $P_2O_6H_3$ or $P_3O_9H_4$.

9. A compound according to claim 1 of structural formula (II):

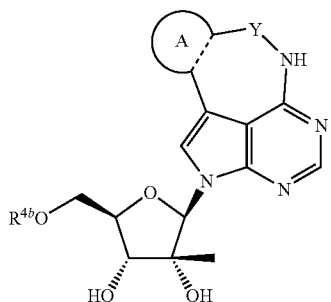

(II)

or a pharmaceutically acceptable salt thereof;
wherein $R^{4b}$ is hydrogen, $C(O)C_{1-10}$alkyl, $PO_3H_2$, $P_2O_6H_3$, $P_3O_9H_4$ or $P(O)R^aR^b$; where $R^a$ and $R^b$ are each independently hydroxy, $OCH_2CH_2SC(=O)C_{1-4}$alkyl, $OCH_2O(C=O)OC_{1-4}$alkyl, OPh, NHCHMeCO$_2$Et, OCH($C_{1-4}$alkyl)O(C=O)$C_{1-4}$alkyl,

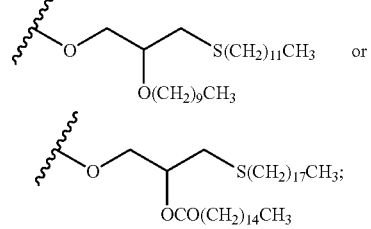

or and ring A is a 5- or 6-membered ring, optionally containing 1 or 2 heteroatoms selected from N, O and S, and containing one, two or three double bonds.

10. A compound according to claim 9 of structural formula (III):

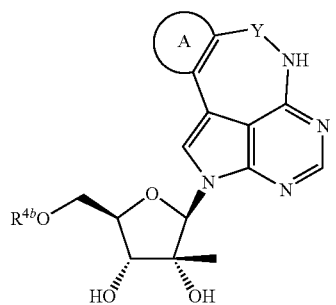

(III)

or a pharmaceutically acceptable salt thereof.

11. A compound according to claim 1, wherein the compound is selected from:

2-(2-C-methyl-beta-D-ribofuranosyl)-2,6-dihydro-7H-2,3,5,6-tetraazadibenzo[C,D,H]azulen-7-one, 2-(2-C-methyl-beta-D-ribofuranosyl)-6,7-dihydro-2H-2,3,5,6-tetraazadibenzo[cd,h]azulene, 2-(2-C-methyl-beta-D-ribofuranosyl)-2,6-dihydro-7H-8-thia-2,3,5,6-tetraazabenzo[CD]cyclopenta[H]azulen-7-one, 2-(2-C-methyl-beta-D-ribofuranosyl)-6,7-dihydro-2H-8-thia-2,3,5,6-tetraazabenzo[CD]cyclopenta[H]azulene, 2-[5-O-(hydroxy{[hydroxy(phosphonooxy)phosphoryl]oxy}phosphoryl)-2-C-methyl-beta-D-ribofuranosyl]-2,6-dihydro-7H-2,3,5,6-tetraazadibenzo[cd,h]azulen-7-one, 2-[5-O-(hydroxy{[hydroxy(phosphonooxy)phosphoryl]oxy}phosphoryl)-2-C-methyl-beta-D-ribofuranosyl]-6,7-dihydro-2H-2,3,5,6-tetraazadibenzo[cd,h]azulene, 2-[5-O-(hydroxy{[hydroxy(phosphonooxy)phosphoryl]oxy}phosphoryl)-2-C-methyl-beta-D-ribofuranosyl]-6,7-dihydro-2H-8-thia-2,3,5,6-tetraazabenzo[c d]cyclopenta[h]azulene, 2-[5-O-(hydroxy{[hydroxy(phosphonooxy)phosphoryl]oxy}phosphoryl)-2-C-methyl-beta-D-ribofuranosyl]-2,6-dihydro-7H-8-thia-2,3,5,6-tetraazabenzo[c d]cyclopenta[h]azulen-7-one, and pharmaceutically acceptable salts thereof.

12. A method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound according to claim 1.

13. A pharmaceutical composition comprising a compound according to claim 1 in association with a pharmaceutically acceptable carrier.

14. A compound according to claim 1 in combination with one or more agents useful for treating HCV infection.

* * * * *